(12) United States Patent
Liu et al.

(10) Patent No.: US 7,440,659 B2
(45) Date of Patent: Oct. 21, 2008

(54) DEPTH-RESOLVED REFLECTANCE INSTRUMENT AND METHOD FOR ITS USE

(75) Inventors: Quan Liu, Durham, NC (US); Nirmala Ramanujam, Janesville, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/708,211

(22) Filed: Feb. 20, 2007

(65) Prior Publication Data
US 2007/0201788 A1    Aug. 30, 2007

Related U.S. Application Data

(60) Provisional application No. 60/777,194, filed on Feb. 27, 2006.

(51) Int. Cl.
*G02B 6/26* (2006.01)

(52) U.S. Cl. .......................... 385/39; 385/15
(58) Field of Classification Search ................ 385/15, 385/39
See application file for complete search history.

(56) References Cited

U.S. PATENT DOCUMENTS

| 5,630,423 | A | 5/1997 | Wang et al. |
| 6,571,118 | B1 | 5/2003 | Utzinger et al. |
| 6,630,673 | B2 * | 10/2003 | Khalil et al. ............. 250/341.8 |
| 6,639,674 | B2 | 10/2003 | Sokolov et al. |
| 6,678,541 | B1 | 1/2004 | Durkin et al. |
| 6,825,928 | B2 * | 11/2004 | Liu et al. ................... 356/317 |
| 6,825,938 | B2 | 11/2004 | Mikami et al. |
| 2005/0143663 | A1 | 6/2005 | Quan et al. |

FOREIGN PATENT DOCUMENTS

WO    WO 02/24048 A    3/2002

OTHER PUBLICATIONS

Carole K. Hayakawa et al, Perturbation Monte Carlo methods to solve inverse photon migration problems in heterogeneous tissues, Sep. 1, 2001/vol. 26, No. 17/pp. 1335-1337/Optics Letters.

Sung K. Chang et al, Analytical model to describe fluorescence spectra of normal and preneoplastic epithelial tissue comparison with Monte Carlo simulations and clinical measurements, Journal of Biomedical Optics 9(3), 511-522 (May/Jun. 2004).

Yasser S. Fawzi et al, Determination of the optical properties of a two-layer tissue model by detecting photons migrating at progressively increasing depths, Applied Optics / vol. 42, No. 31 / pp. 6398-6411 / Nov. 1, 2003.

(Continued)

*Primary Examiner*—Jennifer Doan
(74) *Attorney, Agent, or Firm*—Quarles & Brady LLP

(57) ABSTRACT

A reflectance instrument illuminates the surface of tissue with light of a selected wavelength and light emanating from the tissue due to reflectance is collected. The angle of illumination of tissue surface and/or collection of reflections is changed to probe at various depths beneath the surface of the tissue. The reflectance instrument may be used in a method for measuring the optical properties of a two layer diffuse media such as epithelial tissues.

3 Claims, 10 Drawing Sheets

OTHER PUBLICATIONS

Liu Q, et al., "Sequential Estimation of Optical Properties of a Two-Layered Epithelial Tissue Model from Depth-Resolved Ultraviolet-Visible Diffuse Reflectance Spectra", Applied Optics, OSA, Optical Society of America, Washington D.C., vol. 45 No. 19, Jul. 6, 2006.

Palmer G. M., et al., "Monte Carlo-Based Inverse Model for Calculating Tissue Optical Properties, Part I: Theory and Validation of Synthetic Phantoms", Applied Optics, OSA, Optical Society of America, Washington D.C., vol. 45, No. 5, Feb. 10, 2006.

Hattery, D., et al. "Measuring Oral Inflammation in Vivo With Diffuse Reflectance Spectroscopy", Second Joint EMBS-BMES Conference 2002, Conference Proceedings. 24th Annual International Conference of Engineering in Medicine and Biology Society. Annual Fall Meeting of the Biomedical Engineering Society, Houston, TX, Oct. 23-26, 2002, vol. 1 of 3. Conference 24.

PCT International Search Report.

* cited by examiner

DEPTH-RESOLVED REFLECTANCE INSTRUMENT AND METHOD FOR ITS USE

CROSS-REFERENCE TO RELATED APPLICATIONS

This application is based on U.S. Provisional Patent Application Ser. No. 60/777,194 filed on Feb. 27, 2006 and entitled "DEPTH-RESOLVED REFLECTANCE INSTRUMENT".

STATEMENT REGARDING FEDERALLY SPONSORED RESEARCH

This invention was made with government support under Grant No. CA082710 awarded by the National Institute of Health. The United States Government has certain rights in this invention.

BACKGROUND OF THE INVENTION

The field of the invention is diffuse reflectance spectroscopy and imaging, and in particular, the use of optical reflectance to detect epithelial pre-cancers and cancers. A promising technique under development for squamous epithelial precancer and cancer detection is optical spectroscopy. Optical techniques offer several benefits over traditional diagnostic methods that include visual inspection (through a microscope or endoscope), followed by biopsy. Light can nondestructively interact with a large number of biological molecules intrinsically present in tissues, thus providing a wealth of biochemical and structural information related to disease progression, without the need for tissue removal. Additionally, advances in sensitive detectors and optical fibers make it possible to measure optical signals rapidly and remotely from human tissues in vivo.

There are a large number of absorbers in epithelial tissues in the ultraviolet-visible (UV-VIS) spectral range. The primary absorbers within the cells in the epithelium (top layer of the epithelial tissue) are tryptophan, reduced nicotinamide adenine dinucleotide (NADH), and flavin adenine dinucleotide (FAD). The primary absorber in the underlying stroma is hemoglobin. The primary elastic scatterers in the epithelium are cellular and subcellular components including nuclei and mitochondria, while the primary elastic scatterer in the stroma is collagen.

It has been shown that the endogenous absorption and scattering contrast in precancers and early cancers of stratified squamous epithelial tissues, such as the cervix, varies with depth. Previous microscopy studies on cervical tissue slices and blocks show an increase in the contribution of NADH (source of absorption) within the epithelium, and a decrease in stromal collagen content (source of scattering) with the progression of neoplasia. Researchers have reported increased scattering in the epithelium of precancerous cervical tissues relative to that of normal tissues using confocal microscopy techniques. Moreover, there is increased blood vessel growth (source of absorption) in the stroma with cervical neoplasia, and this has been used by physicians during colposcopy to diagnose cervical precancers.

Diffuse reflectance spectroscopy provides a measure of tissue absorption as well as scattering. Based on the findings described above, depth-dependent absorption and the scattering properties (optical properties) of tissues extracted from diffuse reflectance spectra offer diagnostically useful information for the detection of epithelial precancers and early cancers.

A number of light transport models have been developed to compute optical properties from the diffuse reflectance spectrum measured from a homogeneous medium. However, since squamous epithelial tissues have a layered structure, the use of these simplistic models can cause significant errors in the extracted optical properties. Light transport models for two-layered media can overcome the intrinsic weakness of homogeneous models of light transport.

Several research groups have extended the diffusion theory to calculate the optical properties of a two-layered medium. However, diffusion theory is not valid for highly absorbing media or for small source-detector separations, as is the case in the UV-VIS. Several other research groups have proposed models based on Monte Carlo or hybrid methods. Hayakawa et al. "Peturbation Monte Carlo Methods To Solve Inverse Photon Migration Problems In Heterogeneous Tissues," Opt. Lett. 26, 1335-1337 (2001) developed a perturbation Monte Carlo method to estimate the optical properties of a two-layered medium, in which the perturbation in photon trajectories caused by a small amount of variation in the optical properties relative to baseline values was used to guide a nonlinear optimization algorithm for the estimation of optical properties. The perturbation approach is limited in that it is constrained to small changes in the optical properties (<30% of baseline values for the scattering coefficient), and it requires that the baseline optical properties are known. Chang et al. "Analytical Model To Describe Fluorescence Spectra Of Normal And Preneoplastic Epithelial Tissue: Comparison With Monte Carlo Simulations And Clinical Measurements," J. Biomed. Opt. 9, 511-522 (2004) proposed an analytical two-layered model to describe fluorescence spectra from epithelial tissues measured with a specific probe geometry, in which a single large fiber is used for both light excitation delivery and fluorescence emission collection. By assuming a low scattering epithelium and a highly scattering stroma, as well as one-dimensional light propagation, Beer's law was used to characterize light propagation in the epithelium while the diffusion theory was used to model light transport in the stroma. The analytical form of the model enables fast forward computation of fluorescence emission spectra. However, the presumed probe geometry and limited applicable range of tissue optical properties in each layer limits the utility of this model. Another disadvantage of previously published two-layer models in general is that they contain more free parameters compared to homogeneous models of light transport. The large number of unknowns can dramatically increase the computational time and or even cause the inversion unable to converge.

Fawzi et al. "Determination Of The Optical Properties Of A Two-Layer Tissue Model By Detecting Photons Migrating At Progressively Increasing Depths," Appl. Opt. 42, 6398-6411 (2003) proposed an alternate sequential estimation approach for the determination of optical properties of a two-layered medium. In this approach, a flat-tip probe with a series of small source-detector separations was first used to measure spatially resolved reflectance from the top layer (thickness 5 mm), and a multivariate calibration model was used to extract the top layer optical properties. Then a flat-tip probe with a series of large source-detector separations was used to measure the phase delay and amplitude from both layers (using a frequency domain technique), and the data were fitted to a two layered frequency-domain diffusion model with the estimated top layer optical properties as known inputs. However, since this methodology is based on diffusion theory, it is not appropriate for use in the UV-VIS spectral range and or for small source-detector separations.

SUMMARY OF THE INVENTION

The present invention employs a reflectance instrument and method to characterize the depth dependent reflectance from a target (e.g., pre-cancer or cancer) in a turbid medium (e.g., epithelial tissue). More specifically, the reflectance instrument enables optical properties measurement of a two layered medium in the UV-VIS spectral range to be made separately for each layer, and a first Monte Carlo-based light transport model for a homogeneous medium is used to calculate from these measurements the optical properties of the top layer, and a second Monte Carlo model for a two-layered medium is used to calculate the optical properties of the deeper layer and the thickness of the upper layer.

One aspect of the invention is to provide an instrument which enables the measurement of reflectance from targets at various depths below the surface of a turbid medium such as tissue. This depth-profiling instrument is adaptable to current endoscopic optical imaging systems without significantly increasing their complexity or cost.

Another aspect of the present invention is a method for calculating the optical properties of a two-layer turbid medium which takes advantage of the instrument's ability to resolve the tissue layer from which measurements are made. The measurements from the top layer are used with the first Monte Carlo model to calculate the optical properties of the top layer, and then those calculated properties are used with measurements from the deeper layer to calculate the optical properties of the deeper layer and the thickness of the top layer using the second Monte Carlo model.

A general object of the invention is to measure the optical properties of a two layer turbid medium such as epithelial tissues. These measured optical properties can in turn be used in detecting and diagnosing cancer.

The foregoing and other objects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DESCRIPTION OF THE PREFERRED EMBODIMENTS

Figure 1:
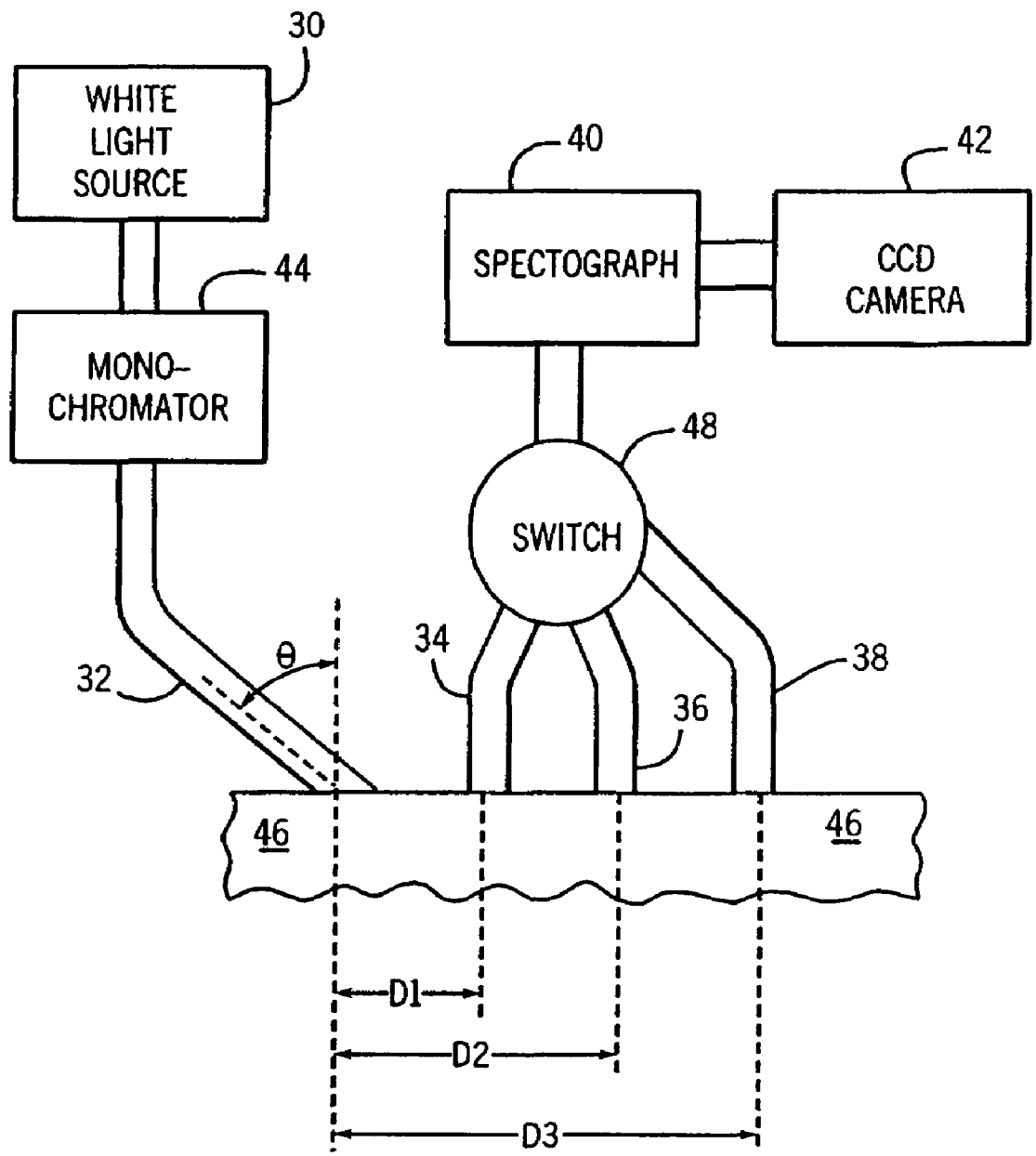
FIG. 1 is a pictorial representation of a reflectance instrument which employs a preferred embodiment of the present invention.

FIG. 1 shows one preferred embodiment of an instrument, which employs the present invention. The primary components are: a filtered white light source 30, an illuminating optical fiber bundle 32, collection optical fiber bundles 34, 36 and 38 and a spectrograph 40 and a detector in the form of a charged couple device (CCD) camera 42. Light emanating from the white light source 30 contains a full spectrum, and a monochromator 44 allows only the light at a selected wavelength to pass through to the illumination bundle 32. The illumination bundle 32 consists of multiple optical fibers, each with the same diameter (200 µm). The illumination light is delivered to the surface of tissue 46 at an incidence angle θ from perpendicular. In the preferred embodiment this angle may be set from 0 to 45.

The collection bundles 34, 36 and 38 are disposed in a line and are placed at different distances from the illumination bundle 32. In the preferred embodiment the collection bundles are spaced at 200 µm center-to-center distances. The collection bundles 34, 36 and 38 are aligned in the direction of the tilted illuminating bundle 32 such that the tissue beneath them is illuminated. The light collected by the collection fibers 34, 36 and 38 is sent to an optical switch 48 which selects the light from one bundle at a time. Measurements of the reflectance at each of the three collection distances $D_1$, $D_2$ and $D_3$ can thus be made in succession by operating the switch 48 and capturing the light. The light collected by the series of collection fibers 34, 36 and 38 is equivalent to light collected at variable aperture sizes. The incident angle θ is also changed to collect light from different depths beneath the tissue surface.

Figure 2:
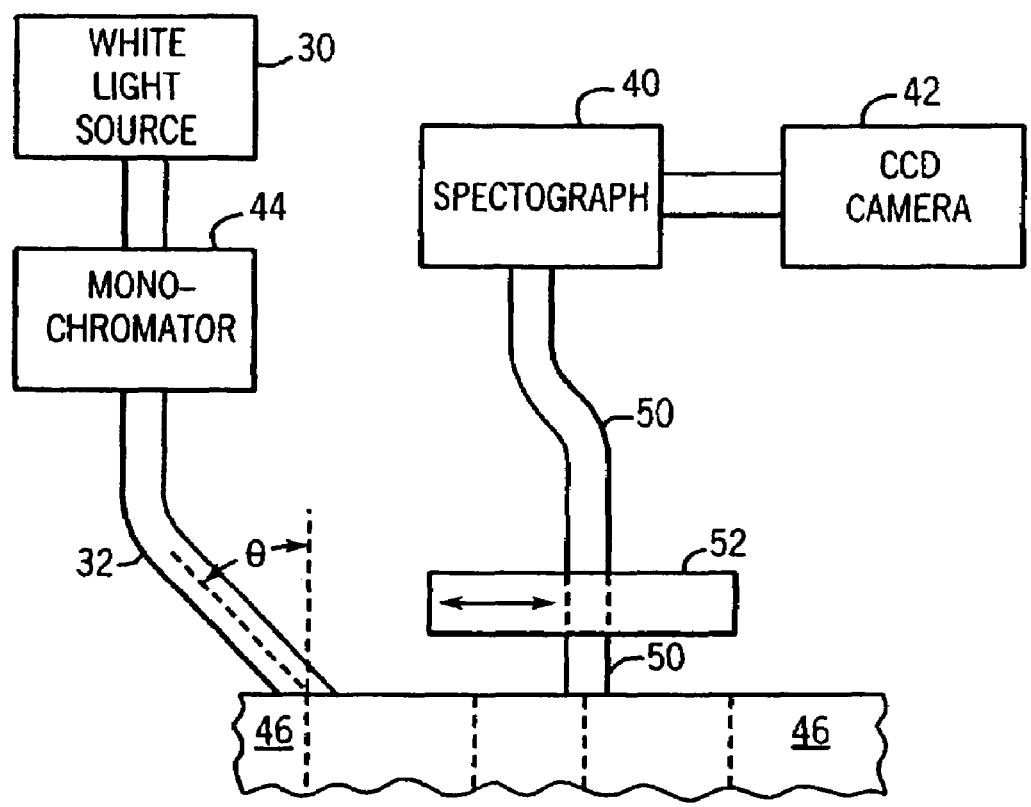
FIG. 2 is a pictorial representation of a reflectance instrument which employs a second preferred embodiment of the present invention.

Another embodiment of an instrument is shown in FIG. 2. This instrument is similar to that described above and shown in FIG. 1 except a single optical fiber collection bundle 50 is employed. No optical switch is therefore needed, but the single collection bundle 50 is moved to different locations on the surface of tissue 46 by a motorized, high resolution translation stage indicated at 52. With this instrument a series of measurements are made with the collection bundle 50 positioned at a corresponding series of locations extending along a path directed away from the illumination bundle 32. These measurements are thus made at a series of different apertures. The incident angle θ is also changed to collect light from different depths beneath the tissue surface.

Figure 3:
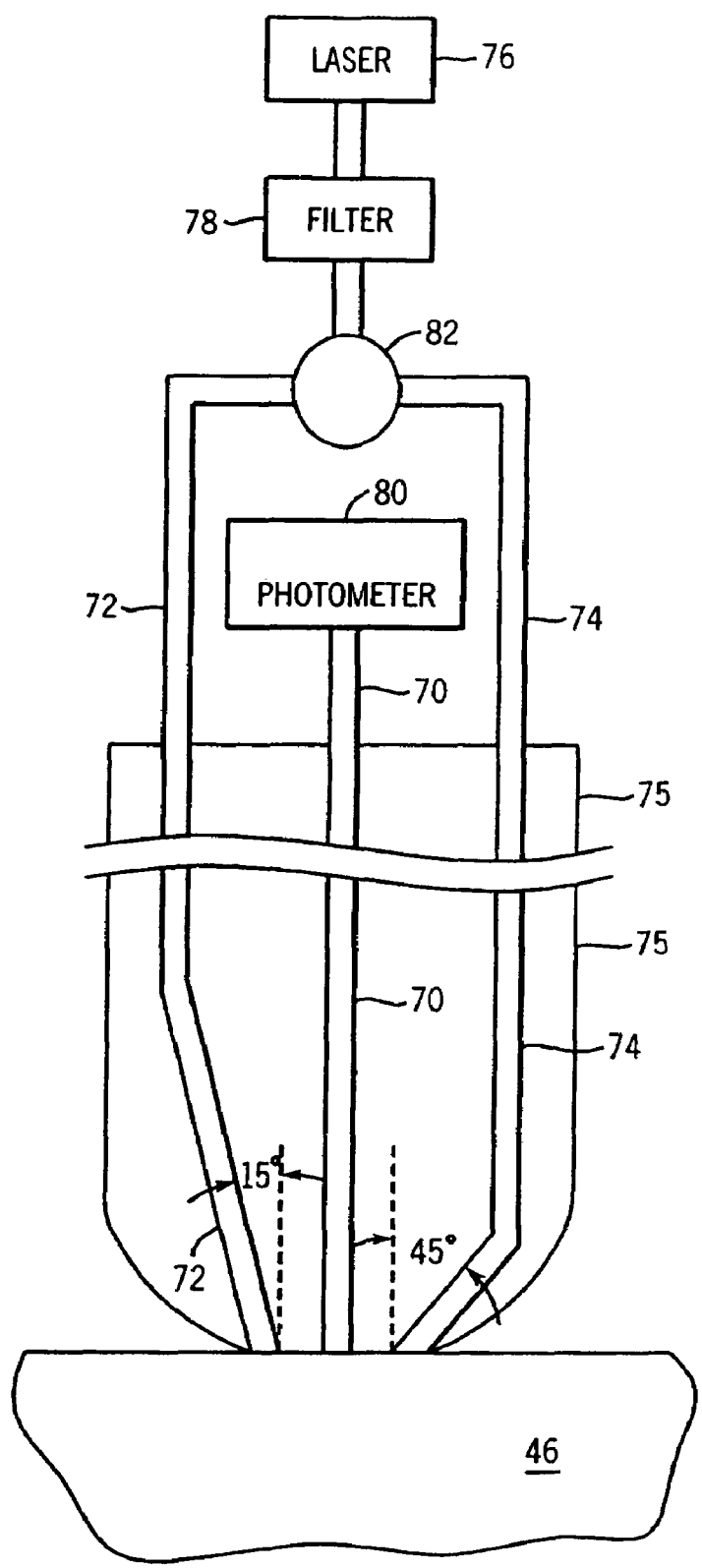
FIG. 3 is a pictorial representation of a reflectance instrument which employs a third preferred embodiment of the present invention.

In a third embodiment of the instrument depicted in FIG. 3, a plurality of illuminating fibers and a single collection fiber are employed. A central collection fiber 70 is fixed perpendicularly to the tissue surface 46, and a pair of illumination fibers 72-74 are disposed on opposite sides of the collection fiber 70. The illumination fibers 72 and 74 are fixed at incidence angles of 15° and 45° respectively with respect to an axis perpendicular to the tissue surface and they are spaced 450 µm from the collection fiber 70. All the fibers have a core diameter of 200 µm and a numerical aperture (NA) of 0.22.

The illumination fibers 72 and 74 are coupled to an argon-ion laser 76 which provides a maximum power of 0.19 W at 351 nm. This output power is attenuated to 1.90 mW by an adjustable aperture and a neutral-density filter 78 before being coupled to the illumination fibers 72 and 74 through a switch 82. The actual output power as measured is 650 μW for the 15° illumination fiber 72 and 300 μW for the 45° illumination fiber 74.

Whereas in the first two embodiments the means for changing the angle of incidence (θ) of the illumination fiber is a mechanism for moving the illumination fiber to the prescribed angle, in the third embodiment the means for changing the angle (θ) is a switch 82. The switch 82 controls which illumination fiber 72 and 74 is energized and hence whether the illumination angle θ is 15° or 45°.

The collection fiber 70 is coupled to the detection module in a photometer 80. The photometer 70 includes a double emission scanning monochromator and a photomultiplier tube.

Figure 4:
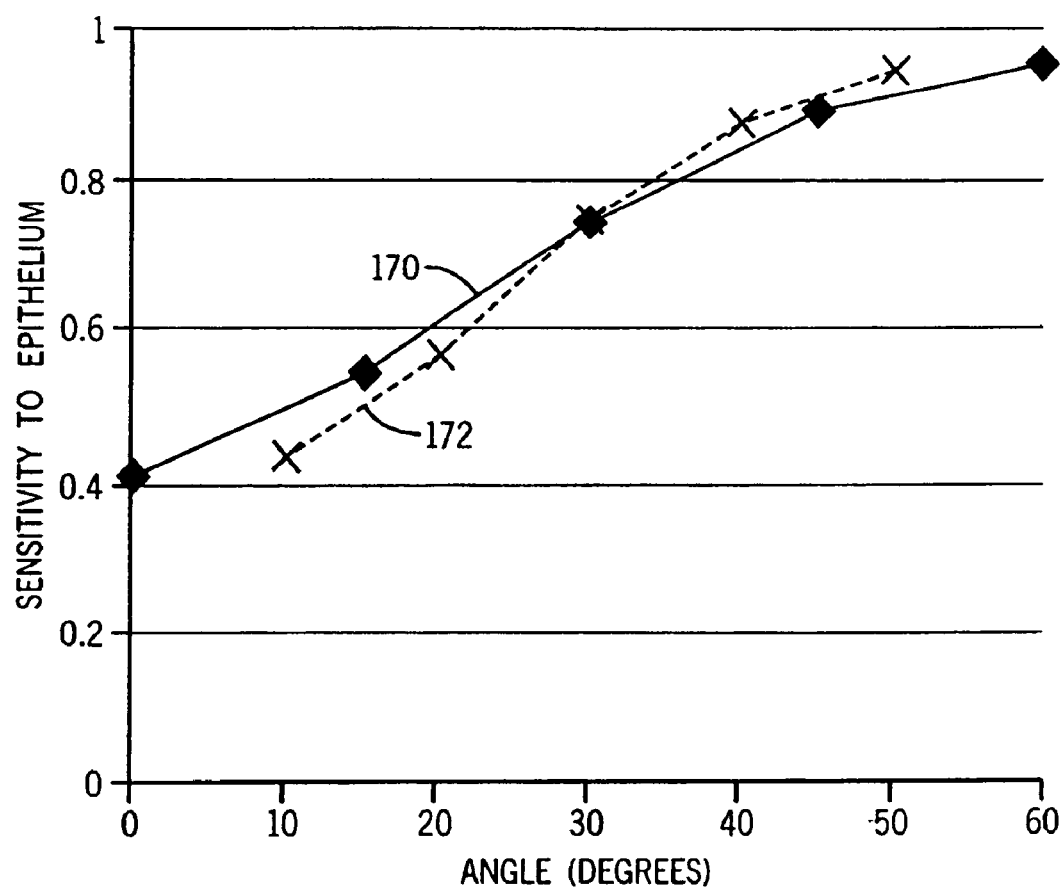
FIG. 4 is a graph indicating the depth sensitivity of the instruments in FIGS. 1-3 as a function of illumination or detection angles.

The above embodiments can be modified such that the detector optical fiber is oriented at different collection angles (θ). This can be done in place of different illumination incidence angles or in addition thereto. As shown in FIG. 4, the change in depth of fluorescence sensitivity as a function of changes in illumination incidence angle is indicated by solid line 170. The corresponding relationship of detection angle to fluorescence depth sensitivity is indicated by dashed line 172 and it can be seen that the relationships are substantially the same. A similar result occurs with reflectance sensitivity.

Figure 5:
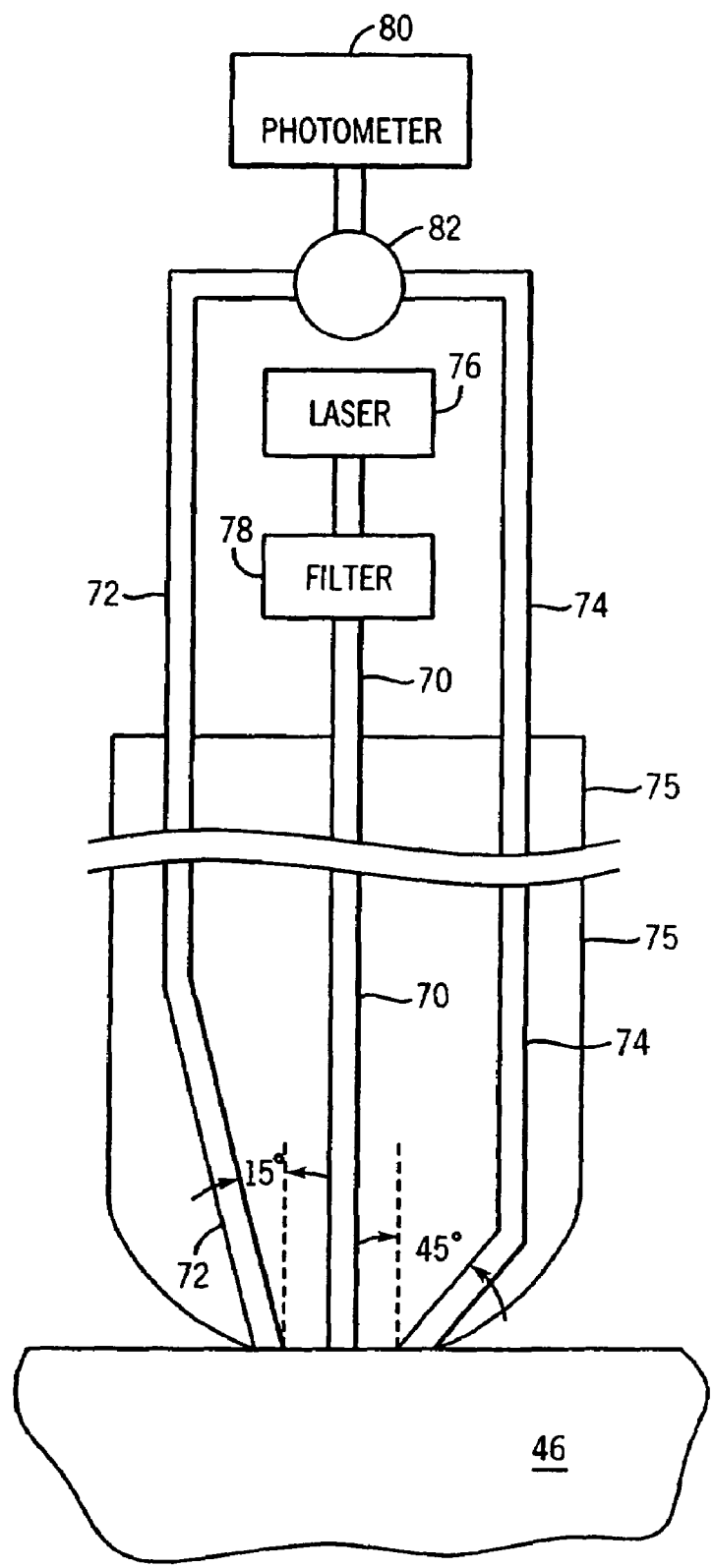
FIG. 5 is yet another preferred embodiment of a reflectance instrument that employs the present invention.

Any of the above-described instruments can be changed to enable detection at different angles rather than illumination at different angles. The illumination device and the detection device need only be switched. Referring to FIG. 5, for example, the optical switch 82 can be connected to the input of the fluorophotometer 80 and the optical fiber 70 connected to the output of filter 78. This results in a single illumination fiber 70 and a pair of detector fibers 72 and 74 that enable the detection angle (θ) to be switched to either 15° or 45°.

While all three of the above described fluorescence instruments can be used to acquire reflectance data at varying depths below a tissue surface, it should be apparent that the embodiment of FIG. 3 is particularly applicable to endoscopic applications because there are no moving parts. In an endoscopic application the two illumination fibers 72 and 74 and the collection fiber 70 are part of an endoscope 75 and they extend from the instrumentation to the distal end of the endoscope 75. They are molded into the fixed, relative positions shown in FIG. 3 at the distal end of the endoscope 75. In use, this distal end is guided to the tissue of interest and pressed against the tissue surface.

Figure 6:
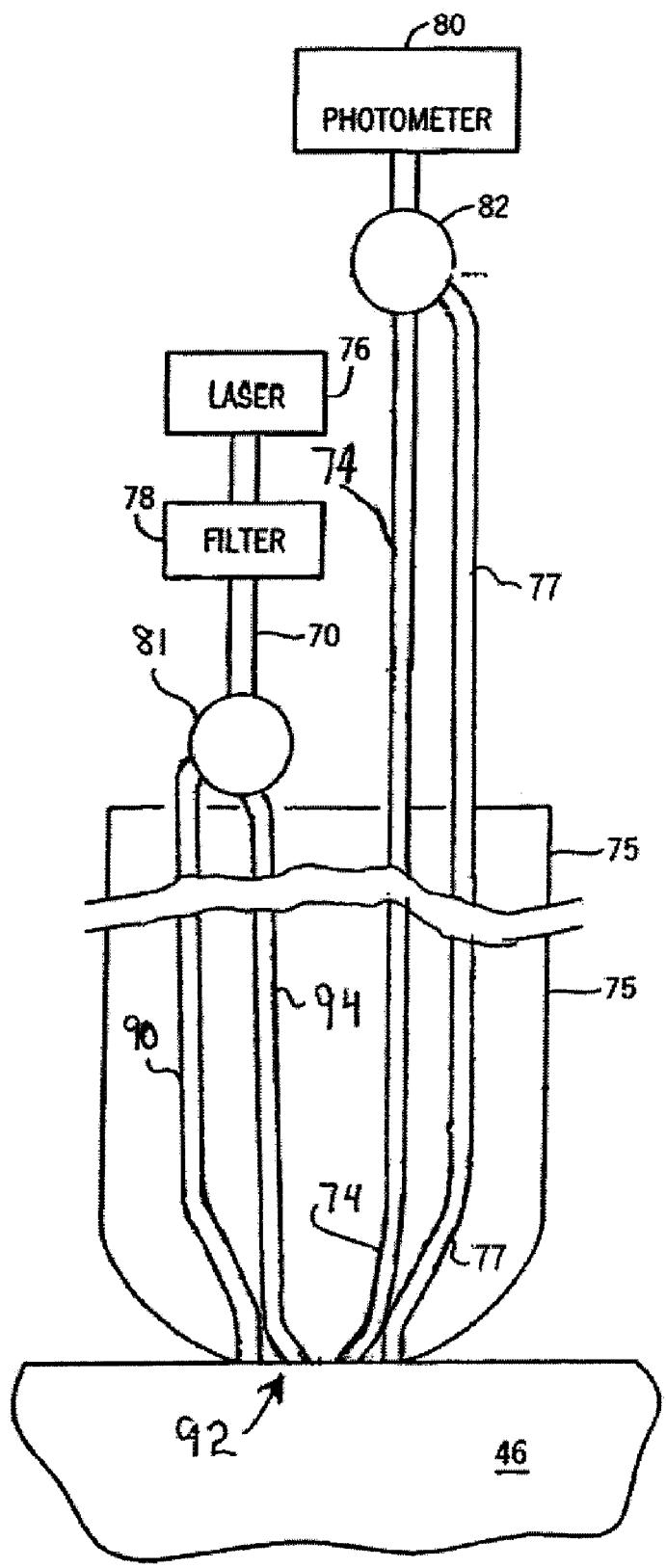
FIG. 6 is a pictorial representation of a reflectance instrument that is employed with the preferred processing method according to the present invention.

Referring particularly to FIG. 6, yet another preferred embodiment of the reflectance instrument is designed for use with a method in which reflectance data is obtained separately from a top tissue layer and a deeper tissue layer. It includes a laser 76 and a filter 78 as described above for producing 0.19 watts at a wavelength of 351 nm on optical fiber 70. An optical switch 81 is operable to direct this light to an optical fiber 90 that extends along the length of a probe 75 and terminates at the probe's distal end 92 that rests against the tissues 46 to be examined. The distal end of the fiber 90 is polished flat and directs the light into the tissue 46 at an angle substantially perpendicular to its surface. As will be explained below, light is applied through optical fiber 90 when deeper layers of tissue are to be examined.

A second optical fiber 94 also connects to an output on optical switch 81, and the distal end of this fiber 94 is angled to convey light into the tissue 46 at an angle of 45° with respect to the tissue surface. As will be explained below, this optical fiber 94 is used when the optical properties of the top layer of tissues is to be examined.

Light which is reflected from within the tissue 46 is picked up by optical fibers 74 and 77 and conveyed to the input of optical switch 82. The switch 82 is operated to couple the light from either the optical fiber 74 or the optical fiber 77 to a photomultiplier 80. The photomultiplier is constructed as described above to detect reflectance from beneath the surface of the tissue 46. The distal end of the optical fiber 74 is disposed at an angle of 45° with respect to the surface of the tissue 46 and the distal end of fiber 77 is polished flat to orient the axis of the fiber 77 perpendicular to the tissue surface.

Figure 7:
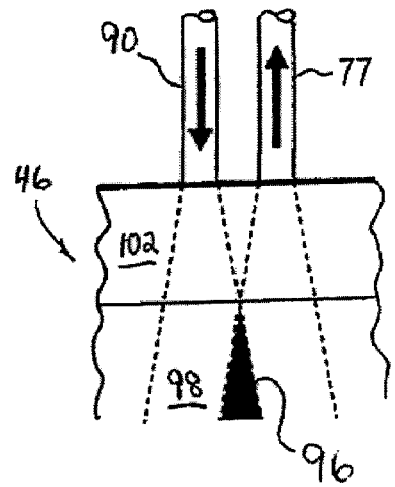
FIGS. 7, 8 and 9 are pictorial representations of the examination regions produced by the instrument of FIG. 6.
Figure 8:
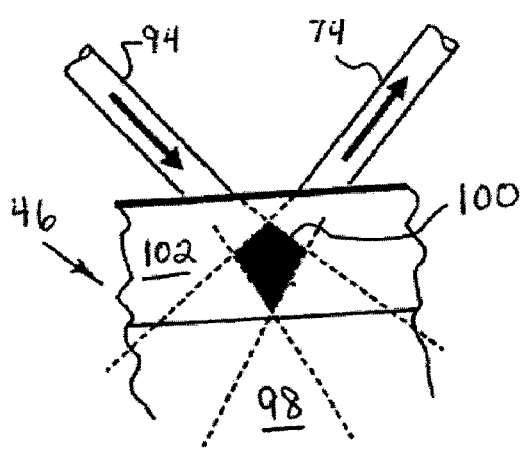
Figure 9:
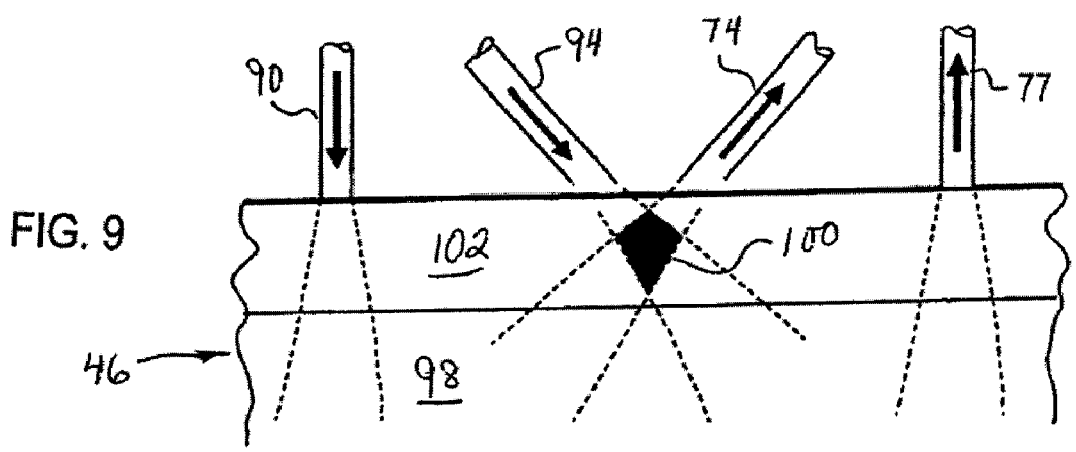

Referring to FIGS. 7-9, the acceptance cones of the illumination optical fibers 90 and 74 and collection fibers 74 and 77 are shown and the arrows indicate light direction. As shown in FIG. 7, the illumination and detection cones of the perpendicular fibers 77 and 90 overlap in a region 96 in a deeper layer 98 of the tissues 46. As shown in FIG. 8, the illumination and detection cones of the angled fibers 94 and 74 overlap in a region 100 located in a top layer 102 of the tissues 46. The complementary attributes of these two probe geometries make them ideally suited to selectively detect diffuse reflectance from the two distinct sublayers of epithelial tissues. The angled probe can be used to detect diffuse reflectance from the superficial epithelial layer, while the flat-tip probe geometry can be used to detect diffuse reflectance primarily from the bottom stromal layer. It should be apparent that the angle of the optical fibers 94 and 74 and the distance between the flat-tip probes 90 and 77 can be changed as a function of the thickness of the superficial epithelial layers being examined.

The instrument in FIG. 6 may be employed with a procedure which measures the diffuse reflectance spectra from the top tissue layer 102 and the deeper tissue layer 98. From these measurements a method such as that now to be described extracts the absorption coefficients $\mu_a$ from both layers, the scattering coefficients $\mu_s$ from both layers and calculates the thickness of the top layer 102.

Figure 10:
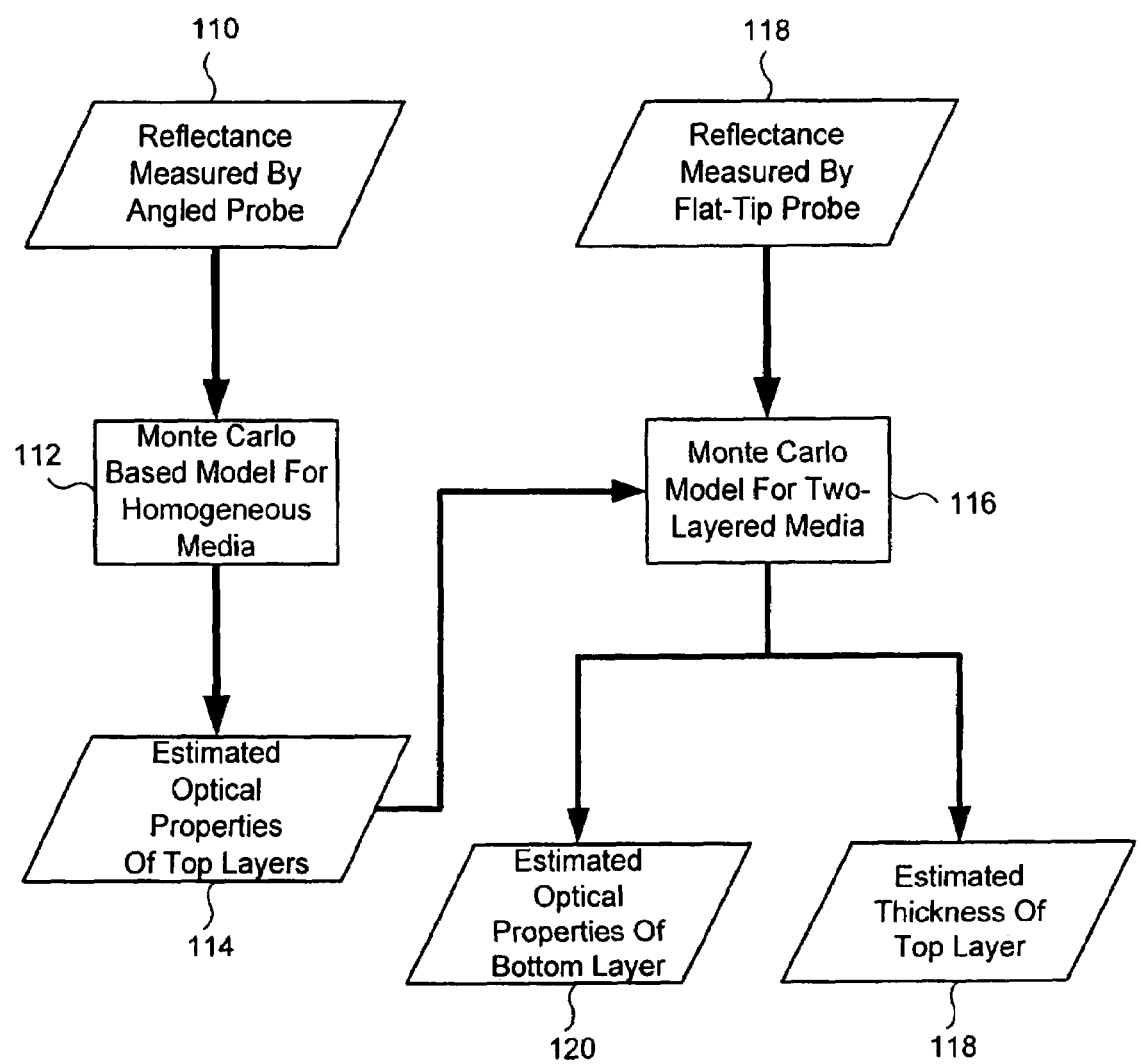
FIG. 10 is a flow chart of the steps in a method for calculating optical properties of two tissue layers.

The steps in this procedure are shown in FIG. 10, and the first step as indicated by input block 110 is to make measurements of the diffuse reflectance spectra using the angled fiber optic probes 94 and 74. This measurement is made by scanning the applied light over a range of wavelengths (e.g., λ=360 nm to 660 nm) and measuring the intensity of the reflected light to produce an optical data set that indicates diffuse reflectance intensity as a function of wavelength λ in the upper layer 102.

This upper layer optical data set is input to a Monte Carlo based process for extracting the scattering coefficient $\mu_s$ and the absorption coefficient $\mu_a$ for the upper layer as indicated at process block 112. This Monte Carlo based process is described in detail in co-pending U.S. patent application Ser. No. 11/119,865, filed on May 2, 2005 and entitled "Method For Extraction Of Optical Properties From Diffuse Reflectance Spectra". The disclosure in this co-pending application is incorporated herein by reference.

Figure 11:
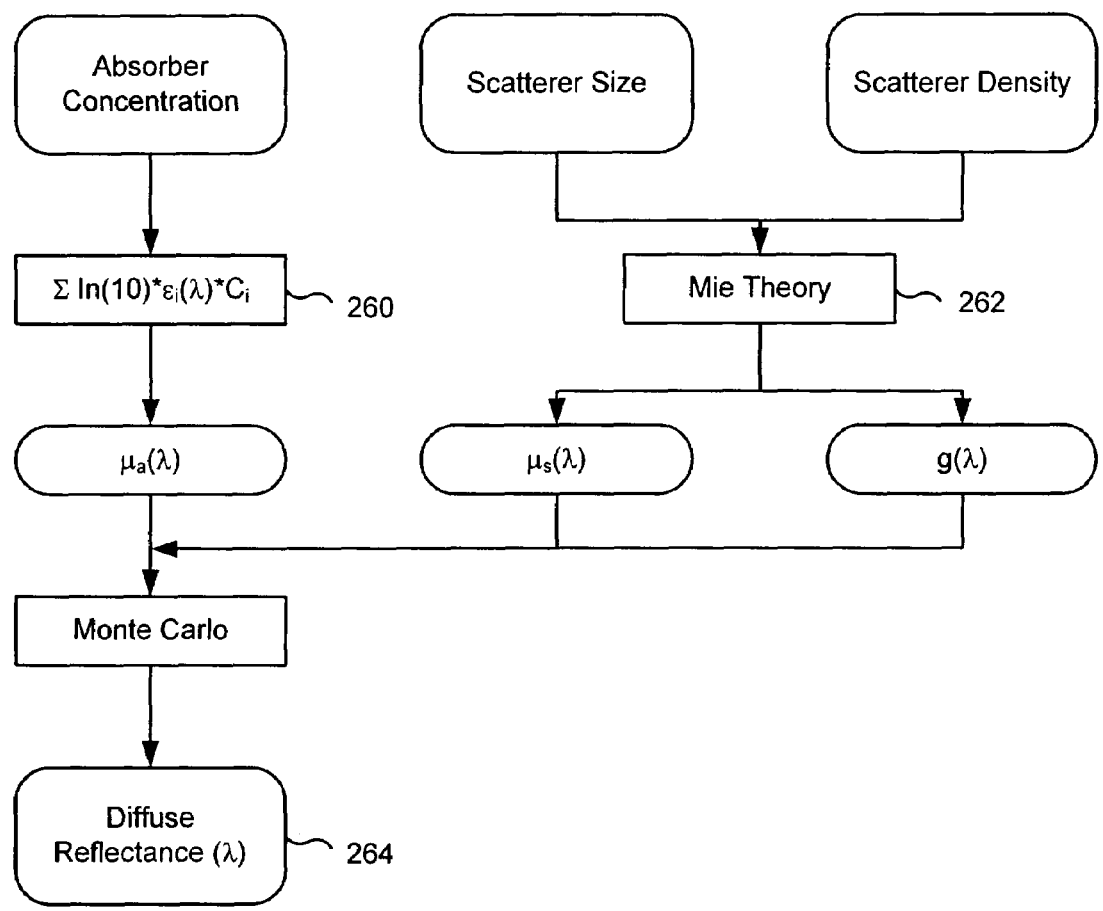
FIG. 11 is a flow chart of a Monte Carlo technique that models a single layer of tissue.

The forward Monte Carlo model refers to the model that relates the physiological and structural properties of the tissue to its measured diffuse reflectance. Referring to FIG. 11, the model has two sets of inputs, which are used to determine the absorption and scattering coefficients, respectively. Beer's law indicated at 260 is used to model absorption. The concentration ($C_i$) of each chromophore (a free optical parameter) and the corresponding wavelength dependent extinction coefficient ($\epsilon_i(\lambda)$) (a fixed optical parameter) are used to determine the wavelength dependent absorption coefficient ($\mu_a(\lambda)$), according to the relationship given by Beer's law, $\mu_a(\lambda) = \Sigma \ln(10) \epsilon_i(\lambda) C_i$. The Mie theory for spherical particles described by C. F. Bohren et al *Absorption and scattering of light by small particles* 1983, New York: Wiley. xiv is used to model scattering as indicated at 262. The scatterer size and density (free optical parameters) and the refractive index being fixed according to known values for phantoms, and expected values for tissue are used to determine the scattering coefficient ($\mu_s(\lambda)$), and the anisotropy factor ($g(\lambda)$) at a given wavelength.

The calculated optical properties ($\mu_a(\lambda)$, $\mu_s(\lambda)$ and $g(\lambda)$) of the tissue can then be input into a Monte Carlo model of light transport to obtain the "modeled" diffuse reflectance for a given wavelength as indicated at 264. The software used for this purpose was adapted from that described by Wang et al. "MCML—Monte Carlo modeling of light transport in multi-layered tissues," Compute Methods Programs Biomed 47, 131 (1995). Note that a Monte Carlo simulation would be required for each unique set of optical properties, thus making this step of the forward model computationally prohibitive. To increase the efficiency of this step a scaling approach such as that described by Graaff et al. "Condensed Monte Carlo simulations for the description of light transport [biological tissue]," Appl Opt 32, 426 (1993) may be employed so that a single Monte Carlo simulation can be run and the output can be scaled to any set of optical properties. The method consists of running a single simulation for a given set of absorption ($\mu_{a,sim}$) and scattering coefficients ($\mu_{s,sim}$), and recording the exit weight ($W_{exit,sim}$), net distance traveled ($r_{t,sim}$), and total number of interactions for each photon (N) that exits the tissue surface. The scaling method then uses these stored parameters to calculate the new exit weight ($W_{exit,new}$) according to Equation (1) and the net distance traveled ($r_{t,new}$) according to Equation (2) for a given photon in the same simulation, but with new tissue absorption ($\mu_{a,new}$) and scattering coefficients ($\mu_{s,new}$). The scaling relationships, taken from Graaff et al., are given below.

$$W_{exit,new} = W_{exit,sim}\left(\frac{\mu_{s,new}}{\mu_{s,new} + \mu_{a,new}} * \frac{\mu_{s,sim} + \mu_{a,sim}}{\mu_{s,sim}}\right)^N \quad (1)$$

$$r_{t,new} = r_{t,sim}\left(\frac{\mu_{s,sim} + \mu_{a,sim}}{\mu_{s,new} + \mu_{a,new}}\right) \quad (2)$$

To further simplify the scaling process, it is assumed that for a given value of the reduced scattering coefficient, $\mu_s' = \mu_s \times (1-g)$, the diffuse reflectance is the same for any value of $\mu_s$ and $g$ that generate the same $\mu_s'$. This has been shown to be valid over the range of $g$ values present in human tissue, i.e., for $g$ values greater than 0.8. Using this similarity relation, and the scaling procedure outlined above, only a single Monte Carlo simulation needs to be run to determine the output diffuse reflectance of a Monte Carlo simulation for any set of optical properties.

The Henyey-Greenstein phase function is used in the single Monte Carlo simulation. The parameters of the single Monte Carlo simulation are as follows: number of photons: 40 million; $\mu_s$: 150 cm$^{-1}$; $\mu_a$: 0 cm$^{-1}$; g: 0.8; model dimensions: 2 cm (radius)×2 cm (depth); refractive indices: 1.33 (medium for phantoms); 1.36 (medium for tissue); and 1.452 (fiber-optic probe above medium in both cases).

A method of convolution is used to integrate over the illumination and collection fibers in order to determine the probability that a photon, traveling a fixed distance, would be collected for a given probe geometry. This takes advantage of the spatial and rotational invariance present in a homogeneous medium. For a pair of illumination and collection fibers, the probability of collection of a photon with a distance $r_t$ between the points of entering and leaving is given by:

$$\frac{1}{\pi^2 r_i^2} \int_{\max(-r_i, s-r_t-r_c)}^{\min(r_i, s-r_t+r_c)} (s-x) \cos^{-1}\left(\frac{s^2 + (s-x)^2 - r_c^2}{2(s-x)s}\right) \cos^{-1}\left(\frac{r_t^2 + (s-x)^2 - r_i^2}{2(s-x)r_t}\right) dx \quad (3)$$

where $r_i$ is the radius of the illumination fiber, $r_c$ is the radius of the collection fiber, s is the separation between the centers of the illumination and collection fibers, and x is the spatial variable over which the integral is taken. This equation is numerically integrated. To adapt this for the fiber bundle in the probe, the common end of the fiber bundle is imaged, and the centers of each illumination and collection fiber in the bundle is determined. Then the probe geometry is integrated pair-wise (for each illumination-collection fiber pair) to determine the total probability of collection.

As indicated at process block 204, the next step is to input a best estimate of tissue optical properties. These values will depend, of course, on the tissues being measured and the particular instrument being used. The optical parameters include "free" parameters such as absorber concentration, scatterer size and scatterer density. Optical parameters also includes "fixed" parameters such as excitation coefficient of the absorber and the refractive index of the scatterer and surrounding medium for each measurement wavelength ($\lambda$). For each measurement wavelength ($\lambda$) a reflectance value Refl $(\lambda)_{model}$ is calculated and stored at process block 208. When the value for the last wavelength ($\lambda$) is calculated as determined at decision block 210, the modeled reflectance values are normalized to the phantom diffuse reflectance spectrum to calibrate for system/wavelength response as indicated at process block 211. A calculation of the sum of squares error is then performed at process block 212. This measures the difference between the measured reflectance values Refl $(\lambda)_{meas}$ for the subject tissue and the corresponding values Refl $(\lambda)_{model}$ predicted by the forward model and then sums the squares of these differences. A Gauss-Newton nonlinear least squares optimization algorithm indicated at process block 214 is employed. This process is in the Matlab optimization toolbox available commercially from the Mathworks, Inc. of Natick Mass. and is used to minimize the error over the course of the iteration process. The free optical parameters are updated at process block 216 and the system loops back to repeat the process and measure the error produced using the newly updated optical parameters. When the trial optical parameters converge with the tissue optical parameters to produce a minimum error at process block 212, the process ends as indicated at decision block 218. The optical parameters $\mu_a(\lambda)$ and $\mu_s(\lambda)$ produced by the forward model using the final trial optical parameters are output as indicated at process block 220. In addition the free optical parameters absorber concentration, scatter size and scatter density my also be output and used for diagnostic purposes. To ensure convergence to a global minimum error, the above procedure may be repeated several times using different sets of initial tissue optical parameters at process block 204.

Referring again to FIG. 10, the optical properties $\mu_a(\lambda)$ and $\mu_s(\lambda)$ of the top tissue layer 102 are output from the above process 112 as indicated at block 114 and input to a second Monte Carlo-based process indicated at process block 116. As indicated at block 118, measurements of the diffuse reflectance spectra of the deeper tissue layer 98 are also made and input to the two layered Monte Carlo-based process 116. These measurements are made using the perpendicular optical fibers 90 and 76 (FIG. 9), and by scanning the applied light over the same range of wavelengths used to measure the top layer 102. The intensity of the reflected light is measured to produce a second optical data set.

Figure 12:
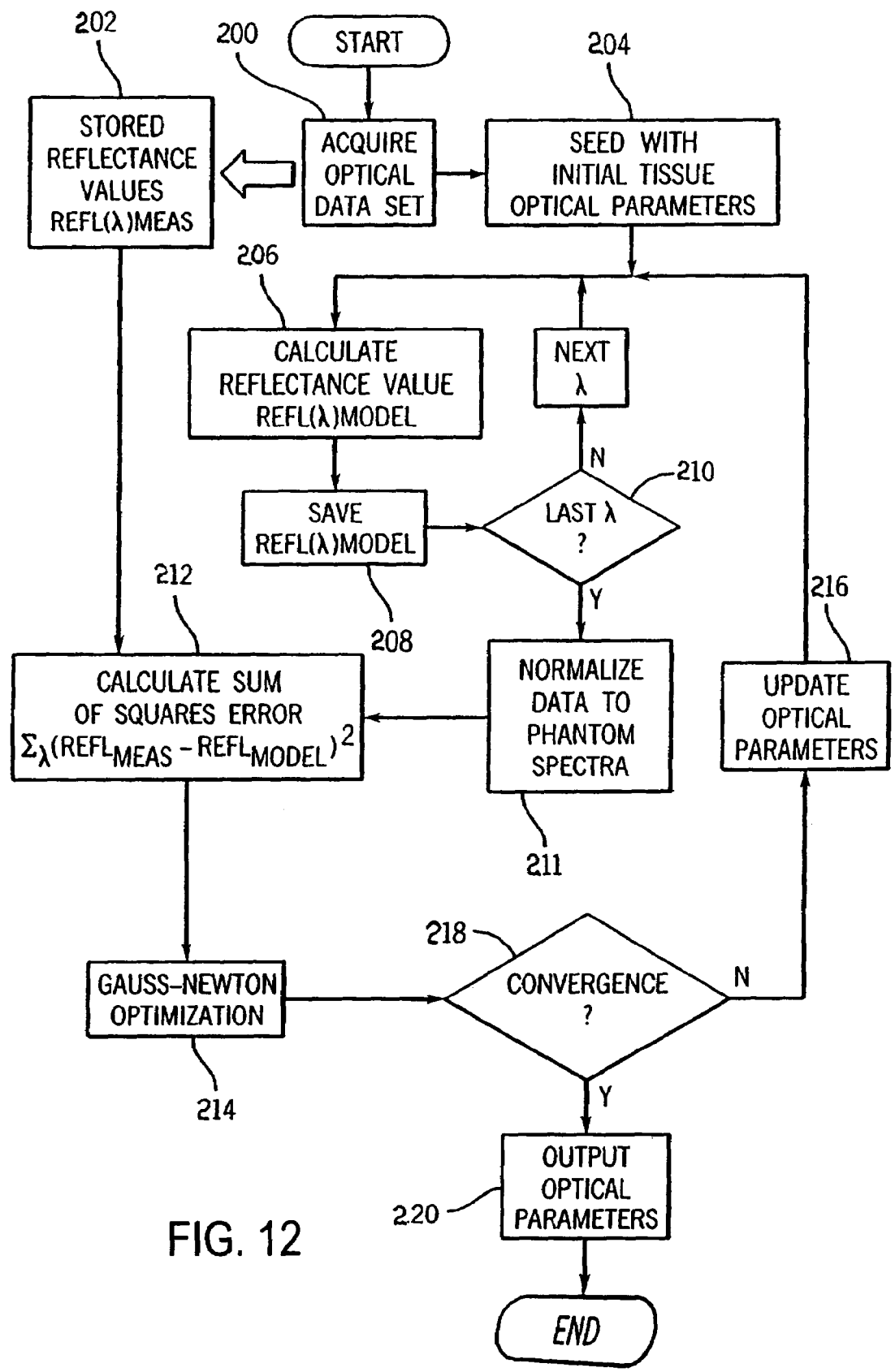
FIG. 12 is a flow chart of an iterative method for using the model of FIG. 11.

A two-layered Monte Carlo model is then used to extract the optical properties of the deeper tissue layer 98 and the thickness of the top tissue layer 102 from the diffuse reflectance spectrum obtained with the flat-tip probe geometry. This two-layered model assumes that the optical properties of the top layer 102 are known from the previous step. In the forward model, Beer's law is used to calculate the absorption coefficient of the bottom layer 98 given the absorber concentration and wavelength-dependent extinction coefficient; Mie theory is used to determine the scattering coefficient of the bottom layer 98 given the scatterer size, density, and refractive index mismatch. Next the optical properties of the two layers 102 and 98 and the thickness of the top layer 102 are used as inputs into the two-layered Monte Carlo model to generate a predicted diffuse reflectance. The inversion approach used is the same as that described above and shown in FIGS. 11 and 12, except the optical properties being retrieved are for the deeper rather than the top layer, and the thickness of the top layer is included as an additional free parameter.

A different approach is used to increase the efficiency of the two-layered forward Monte Carlo model. Specifically, a series of baseline Monte Carlo simulations are run ahead of time to generate a database of diffuse reflectance values for a two-layered medium for zero absorption and a wide range of scattering coefficients of the top and bottom layers. For each scattering coefficient pair (top and bottom layers), simulations were carried out for a range of thicknesses. Table 1 lists the reduced scattering coefficients and thicknesses of the top and bottom layers used in the baseline simulations to generate the Monte Carlo database for two-layered media.

TABLE 1

Scattering Coefficients and Thicknesses of the Top and Bottom Layers Used in the Baseline Simulations to Generate the Monte Carlo Database for Two-Layered Media

|  | Top Layer | Bottom Layer |
|---|---|---|
| Reduced scattering coefficient, $\mu_s'$ (cm$^{-1}$) | 3, 3.67, 4.48, 5.48, 6.69, 8.18, 10.00, 12.22, 14.94 | 14, 17.11, 20.91, 25.56, 31.24, 38.18, 46.67 |
| Thickness (μm) | 0, 50, 100, 150, 200, 250, 300, 350, 400, 500, 600, 700, 800 | 30 000 |

The anisotropy factor was 0.9, and the absorption coefficient was zero in all simulations. All combinations of the listed parameters were used. A total of 819 independent simulations were run, each with 1×10$^7$ incident photons. To reduce the variance of the detected diffuse reflectance, photons were collected over a ring area around the central axis of the illumination fiber, the radial thickness of which was equal to the diameter of the collection fiber. During each simulation, the path length of every detected photon in each of the two layers was recorded. The diffuse reflectance as a function of the radial distance of the photon's exit location was then scaled for a given absorption coefficient using Beer's law (which is a function of the absorption coefficient and the path length) and for the actual fiber collection area. Linear interpolation was used to calculate the diffuse reflectance for optical properties or thicknesses not contained in the database. The results were compared to those directly obtained from independent simulations to validate the accuracy of this approach.

The two-layered Monte Carlo-based process 116 produces the optical properties $\mu_a(\lambda)$ and $\mu_s(\lambda)$ of the deep layer 98 which is output at 120, and it calculates the thickness of the top tissue layer 102 which is also output at 118.

While the method for measuring the optical properties of two tissue layers has been described with respect to the instrument shown in FIG. 9, it should be apparent that any of the above described instruments may be used. The choice in some cases will be determined by the particular clinical application and in other cases by the thickness of the two tissue layers being measured.

The invention claimed is:

1. A method for calculating the scattering and absorption characteristics of two layers of tissue, the steps comprising:
    a) acquiring a first set of diffuse reflectance measurements from a top layer of said two layers of tissue using an instrument which limits the reflectance measurements to a shallow depth beneath the surface of the tissue;
    b) calculating the absorption coefficient $\mu_a$ and scattering coefficient $\mu_s$ of the top layer of tissue using the measurements acquired in step a);
    c) acquiring a second set of diffuse reflectance measurements from a deeper layer of said two layers of tissue using an instrument which limits the reflectance measurements primarily to a depth below the top layer of tissue; and
    d) calculating the absorption coefficient $\mu_a$ and scattering coefficient $\mu_s$ of the deeper of said two tissue layers and the thickness of the top tissue layer using the top layer coefficients calculated in step b) and the diffuse reflectance measurements acquired in step c).

2. The method as recited in claim 1 in which step b) is performed using a single layer model of tissue and step d) is performed using a two layer model of tissue.

3. The method as recited in claim 2 in which the models used in steps b) and d) are Monte Carlo-based models.

* * * * *